United States Patent [19]

Jones

[11] Patent Number: 4,637,259

[45] Date of Patent: Jan. 20, 1987

[54] FATIGUE TEST MACHINE

[75] Inventor: David I. G. Jones, Dayton, Ohio

[73] Assignee: The United States of America as represented by the Secretary of the Air Force, Washington, D.C.

[21] Appl. No.: 805,518

[22] Filed: Dec. 6, 1985

[51] Int. Cl.⁴ .............................................. G01N 3/00
[52] U.S. Cl. ...................................... 73/794; 73/802
[58] Field of Search ............... 73/794, 795, 796, 797, 73/798, 799, 802, 806, 808, 810, 813, 814, 816, 577, 578, 856, 860

[56] References Cited

U.S. PATENT DOCUMENTS

| | | | |
|---|---|---|---|
| 1,583,877 | 5/1926 | Hahnemann et al. | 73/578 |
| 2,844,958 | 7/1958 | Bennett et al. | 73/860 |
| 3,442,120 | 5/1969 | Russenberger et al. | 73/577 |
| 3,563,086 | 2/1971 | Reed, Jr. | 73/92 |
| 3,575,045 | 4/1971 | Knights | 73/92 |
| 4,026,142 | 5/1977 | Jacobs | 73/577 |

Primary Examiner—Jerry W. Myracle
Assistant Examiner—Robert R. Raevis
Attorney, Agent, or Firm—Charles E. Bricker; Donald J. Singer

[57] ABSTRACT

A fatigue testing machine for testing materials under combined static and dynamic loads. The machine comprises a right circular ring, a pair of specimen clamps adapted for slidably fitting into diametrically opposed openings in the ring, a support cradle for the ring and a shaker. The clamps comprises means for applying a static load to a specimen clamped therebetween.

3 Claims, 5 Drawing Figures

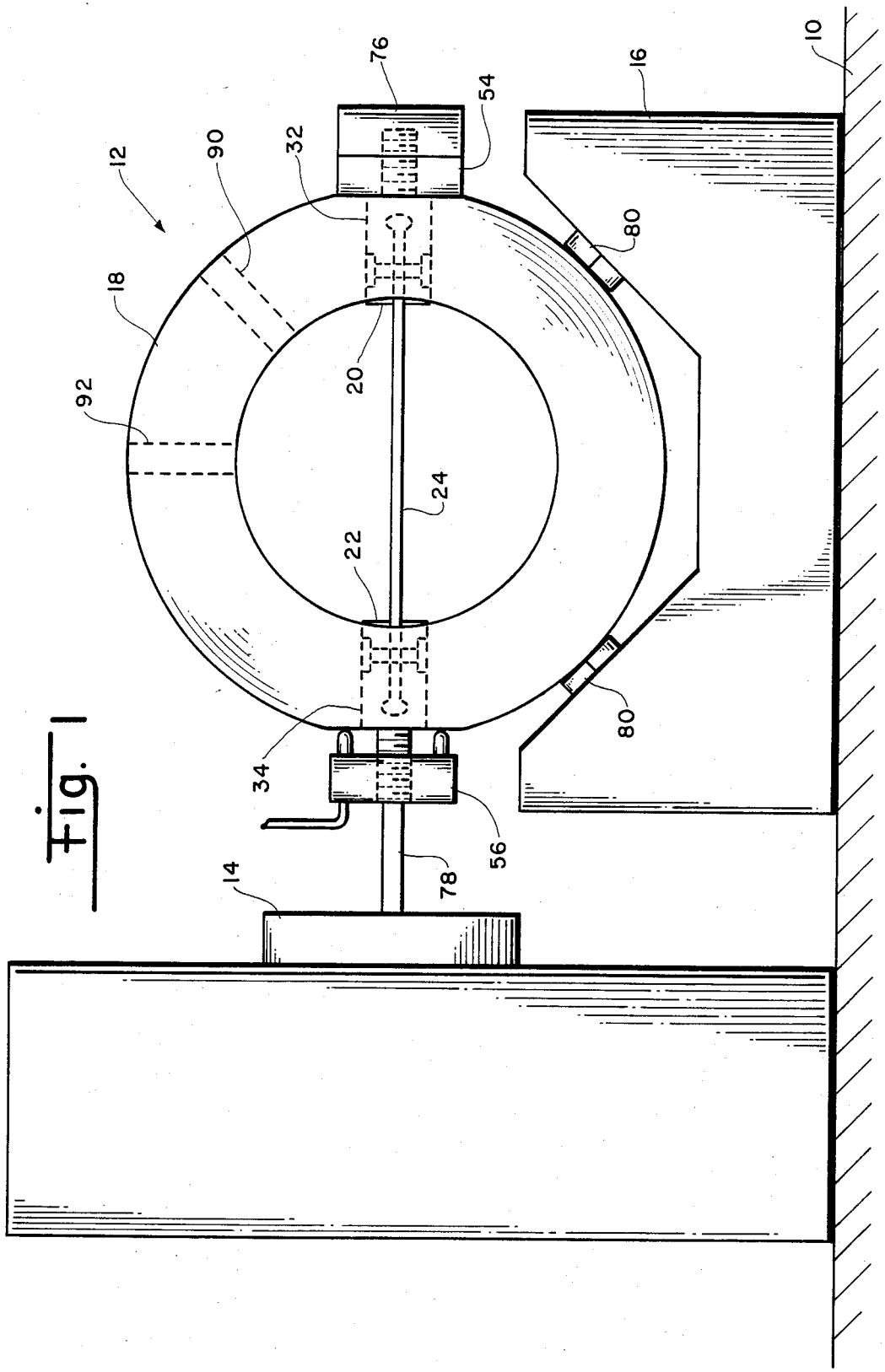

FATIGUE TEST MACHINE

RIGHTS OF THE GOVERNMENT

The invention described herein may be manufactured and used by or for the Government of the United States for all governmental purposes without the payment of any royalty.

BACKGROUND OF THE INVENTION

This invention relates to an apparatus for testing materials under combined static and dynamic loads.

Materials used in rotating components of, for example, jet engines are subjected to unusually severe environmental conditions during their operational lifetimes. Components such as disks and blades are subjected to high temperature excursions, high levels of "steady" stress from centrifugal loads (low cycle stress), as well as high levels of high frequency "dynamic" stress from resonant vibration response (high cycle stress). The thermal-mechanical cycling of the component material can lead to initiation and propagation of cracks at voids, defects or scratches. The crack initiation and propagation characteristics of materials used in jet engine components vary widely, according to whether the material is more or less ductile, and depend on temperature, low cycle stress, high cycle stress, frequency, dwell time, local atmospheric conditions and many other parameters. Test methods to obtain data vary widely, but are generally limited in one way or another. In particular, few test systems can independently vary low cycle and high cycle loads over a wide frequency range, even in accordance with a simplified cycle, such as (1) apply low cycle load, (2) apply high cycle load, (3) discontinue high cycle load, and (4) discontinue low cycle load. Most test systems are limited to loads of a few hundred hertz. For example, many servo-hydraulic systems can combine low cycle loads with high cycle loads at frequencies up to 10 or 20 Hz. A few systems can operate at frequencies up to about 500 Hz, or marginally higher. However, none of these systems is simple or low in price. There exists a need for a simple, low-cost fatigue test system for investigating crack initiation and propagation behavior in test specimens under combined low cycle and high cycle loading, which can operate at very high frequencies.

Accordingly, it is an object of the present invention to provide a novel fatigue test system which satisfies the above-stated need.

Other objects, aspects and advantages of the invention will be apparent to those skilled in the art.

DESCRIPTION OF THE DRAWINGS

In the drawings,

FIG. 1 is an elevation showing the testing apparatus of the invention;

DESCRIPTION OF THE PREFERRED EMBODIMENTS

Figure 3:
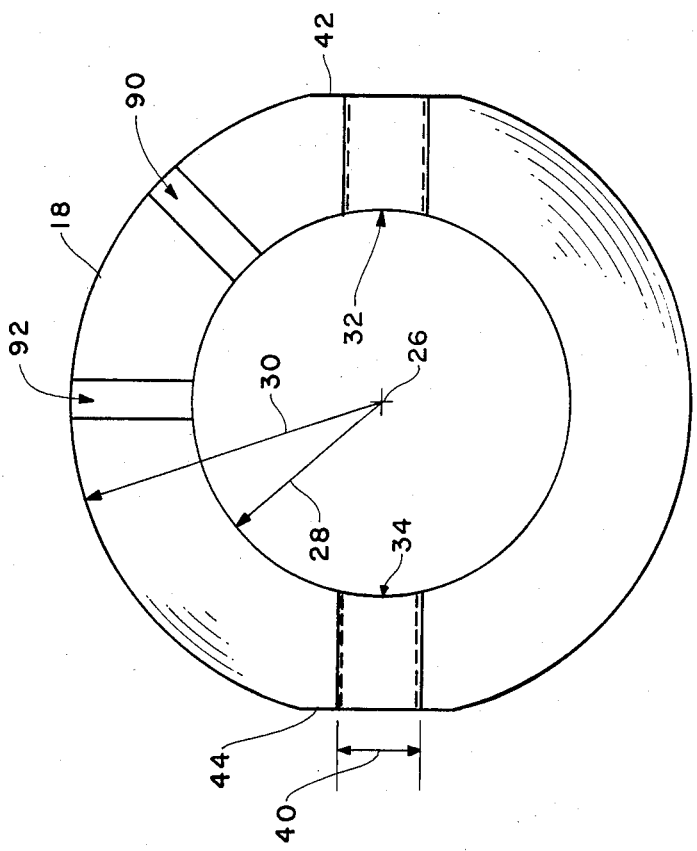
FIG. 3 is a cross-section of the test ring taken through 3—3 of FIG. 2.

Referring to FIG. 1, there is shown an elevation of the general assembly of the apparatus of this invention.

A suitable base 10 is provided for supporting the fatigue test apparatus of this invention.

The test apparatus is designated generally by reference numeral 12; its associated shaker is designated by numeral 14. The test apparatus 12 comprises a support cradle 16, a right circular ring 18, a first specimen clamp 20 and a second specimen clamp 22. Also shown is a strip specimen 24 clamped between clamps 20 and 22.

Figure 2:
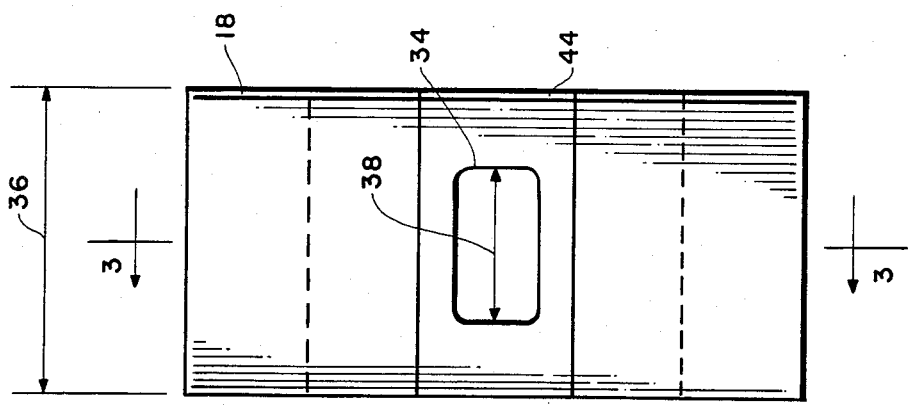
FIG. 2 is an end view of the test ring.

Referring to FIGS. 2 and 3, the ring 18 has a central axis 26, an inside radius 28, an outside radius 30, a first radial passage 32, a second radial passage 34, and a height 36. Each of the radial passages 32 and 34 has a dimension 38 parallel to axis 26 of not greater than about 70% of the height 36 of ring 18 and a vertical dimension 40 not greater than about 70% of the height 36. Portions of external surface of ring 18 surrounding the openings to the passages 32 and 34 may be ground or machined flat, as indicated at 42 and 44, respectively.

Figure 4:
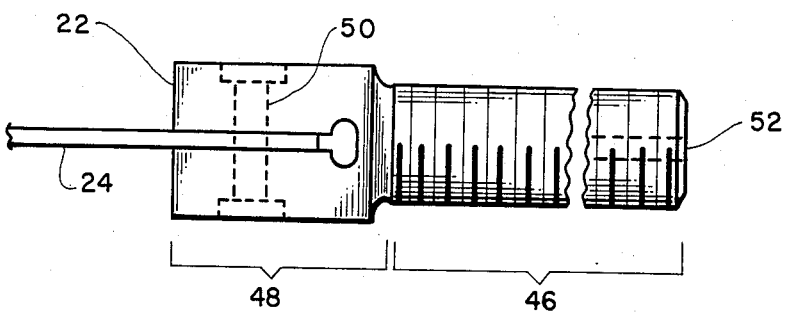
FIG. 4 illustrates a specimen clamp.

A specimen clamp 22 is shown in FIG. 4, with a specimen 24 clamped in place. Clamp 20 may be identical to clamp 22. Clamp 22 has a threaded portion 46 and a bore-fit portion 48, the latter being adapted to be slidably received in a radial passage 32 or 34 in ring 18. The bore-fit portion 48 comprises one or more drilled-through holes 50 for receiving therein bolts for clamping the specimen 24 in the clamp 22. The thread portion 46 has a drilled and threaded axial hole 52.

Referring again to FIG. 1, a specimen 24 is clamped into clamps 20 and 22, and this assembly is inserted through passages 32 and 34. A nut 54 is threaded onto the threaded portion of clamp 20. A hydraulic loader 56 is threaded onto the threaded portion of clamp 22.

Figure 5:
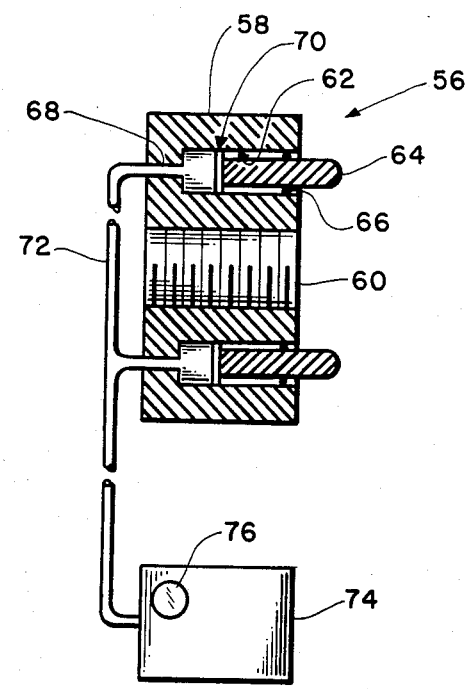
FIG. 5 illustrates a hydraulic loading device for static loading a test specimen.

The hydraulic loader 56 as shown in FIG. 5 comprises a block 58 having a centrally-located threaded bore 60 and a plurality of hydraulic rams, each such ram comprising a cylindrical chamber 62, a ram member 64, at least one sealing member 66 and conduit means 68 for introducing a hydraulic fluid into the chamber 62. The ram member 64 comprises an engaging portion 70 adapted to closely, yet slidably fit the bore of chamber 62. Each of the chambers 62 is connected, through conduit means 68 and external tubing 72 to a hydraulic power supply and controller means 74, which includes a pressure gage 76.

Referring again to FIG. 1, once the loader 56 is threaded onto clamp 24, hydraulic power is applied by the supply and controller means 74 to actuate the rams 64, thereby applying a static tension across the sample 24. Alternatively, a nut 54 can be threaded onto the threaded portion of clamp 22 and this nut, as well as the nut 54 on clamp 20, can be turned manually to apply the desired static load to sample 24. In the embodiment shown, an accelerometer 76 is threaded onto the threaded portion of clamp 20. Finally, the end actuator rod 78 of shaker 14 is threaded into the threaded hole 52 in clamp 22.

Support cradle 16 is adapted to support ring 18 at points corresponding to the null points of a cylindrical shell vibrating in its low order modes. For the N=2 mode, the support points are at ±45° relative to the positions of clamps 20 and 22. Each of the support points is provided with isolation pads 80 made of natural or synthetic elastomeric material for preventing or at least considerably diminishing transfer of vibration from ring 18 to cradle 16.

When driven by shaker 14 the ring 18 has a theoretical resonant frequency $f_N$, corresponding to the order N of the mode, given by the approximate expression:

$$f_N = \frac{1}{2\pi} \sqrt{\frac{EH^2N^2(1-N^2)^2}{12\rho R^4(1-\nu^2)(1+N^2)}} \quad (1)$$

where $f_N$ is expressed in Hz, E is Young's modulus for the ring material, H is the thickness of the ring (outer radius—inner radius), R is the average radius of the ring, $\rho$ is the density of the ring material and $\nu$ is Poisson's ratio.

Specimen testing may be carried out at temperatures below and above room temperature by placing the apparatus in a suitable temperature-controlled chamber. For testing specimens at temperatures greater than about 300° F. (150° C.), it is preferred that only the specimen be heated, such as by the use of induction heating.

The following example illustrates the invention:

An apparatus following the above teaching was constructed and tested. The ring 18, fabricated from mild steel having a density of 0.3 lb/cu-in, had an outside radius 30 of 4.0 in., a height 36 of 4.0 in. and an inside radius 28 of 2.5 in. Entering these dimensions into Equation (1) provides the following theoretical resonant frequencies:

$f_2 = 3,648.3$ Hz.
$f_3 = 10,318.9$ Hz.
$f_4 = 19,785.7$ Hz.

Radial observation ports 90 and 92 were cut through the ring 18 at points +45° and +90°, respectively, relative to radial passage 32 for observing a specimen under test. It was later determined that these ports were not necessary; that the specimen could be adequately observed from the side.

The apparatus, without a specimen in place, was excited by a 50-lb (rating) electrodyanmic shaker. The force was measured at the excitation point by a force gage and the response was picked up by a miniature accelerometer placed at various points on the ring. Compliance spectra were measured by a digital sine-sweep test system. The N=2 mode occurred at a frequency of about B 2850 Hz, which is lower than the expected frequency $f_2$ of 3648.3 Hz, the lower resonant frequency being due, at least in part, to the cut-through observation ports 90 and 92 and the two radial passages 32 and 34 for specimen clamps 20 and 22 in ring 18.

The force spectrum (force amplitude vs. frequency) of ring 18 was measured using a force gage at a fixed shaker input current. The measured force was high up to about 1800 Hz, but dropped rapidly thereafter, being down about 10 db at the frequency of the N=2 mode. The dropoff after 1800 Hz is due primarily to the force needed to accelerate the shaker table.

Specimen tests were conducted using a specimen 1 inch wide by 0.093 inch thick. Static tension in the specimen was set manually to correspond to a torque of about 300 in-lb at the nut 54. For these tests a nut 54 was used instead of the hydraulic loader 56 shown in FIG. 1. Response spectra of this system indicated a major peak near 2500 Hz, corresponding to the N=2 mode, this lower frequency being due, at least in part, to the weight of nuts 54.

The shaker input was applied at the maximum level attainable at the resonance frequency of 2500 Hz. The maximum acceleration measured at each end of the specimen was about 180 g's (peak). The relative high cycle frequency excursion of the specimen across the ring diameter was calculated to be $5.61 \times 10^{-4}$ in. For a ring mass of 36.8 lb and an assumed modal loss factor of 0.005 the driving force amplitude was calculated to be 16.56 lb. The calculated force of 16.56 lb is about 10 db below the nominal maximum of 50 lb, but agrees quite well with the earlier-obtained (without specimen) force spectrum. The maximum stress in the specimen was calculated to be 3365 lb/sq-in.

Various modifications may be made without departing from the spirit of the invention described or the scope of the appended claims.

I claim:

1. A fatigue testing apparatus for testing a specimen under combined low cycle and high cycle loading which comprises: a test fixture, means for supporting said test fixture and means for applying a dynamic load to said test fixture, wherein said test fixture consists essentially of:
    (a) a right circular cylinder having:
        an inside diameter, an outside diameter, a height and a central axis;
        a first radial opening in said cylinder, said opening having a height dimension parallel to said central axis not greater than about 70% of said cylinder height and a circumferential dimension not greater than about 70% of said cylinder height, and
        a second radial opening in said cylinder diametrically opposite said first opening, said second opening having substantially the same dimensions as said first opening;
    (b) a pair of specimen clamping means having:
        a first portion adapted to slidably fit into said radial openings in said cylinder,
        said first portion comprising means for receiving and clamping a specimen, and a second portion comprising means to limit the travel of said clamping means into said radial openings toward said central axis,
        wherein at least one of said clamping means further comprises means for applying a static pressure to a specimen clamped between said clamping means,
        wherein one of said clamping means further comprises means for connection to said dynamic load-applying means; and
        wherein said supporting means comprises means to support said cylinder at at least two nodal points for a desired mode of vibration at a resonant frequency defined by the formula $$f_N = \frac{1}{2\pi} \sqrt{\frac{EH^2N^2(1-N^2)^2}{12\rho R^4(1-\nu^2)(1+N^2)}} \quad (1)$$

where N is an integer corresponding to the mode of vibration, E is Young's modulus, N is the mode number, $\rho$ is the density of the material of said cylinder, $\nu$ is Poisson's ratio, H is the thickness of said cylinder and R is the average radius of said cylinder.

2. The apparatus of claim 1 wherein said load applying means is an electrodynamic shaker.

3. The apparatus of claim 1 wherein said static pressure applying means is a hydraulic loader.

* * * * *